United States Patent
Jones (10) Patent No.: US 9,623,187 B2
(45) Date of Patent: Apr. 18, 2017

(54) RESETTABLE DRUG DELIVERY DEVICE

(75) Inventor: Christopher John Jones, Broadway (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 1094 days.

(21) Appl. No.: 12/788,678

(22) Filed: May 27, 2010

(65) Prior Publication Data

US 2010/0324495 A1  Dec. 23, 2010

Related U.S. Application Data

(60) Provisional application No. 61/182,831, filed on Jun. 1, 2009.

(30) Foreign Application Priority Data

Jul. 10, 2009   (EP) .................................... 09009053

(51) Int. Cl.
*A61M 5/31* (2006.01)
*A61M 5/315* (2006.01)
*A61M 5/24* (2006.01)

(52) U.S. Cl.
CPC .......... *A61M 5/31535* (2013.01); *A61M 5/24* (2013.01); *A61M 5/31543* (2013.01); *A61M 5/31551* (2013.01); *A61M 5/31585* (2013.01); *A61M 2005/2488* (2013.01)

(58) Field of Classification Search
CPC ................ A61M 5/24; A61M 5/31543; A61M 5/31551; A61M 5/31585; A61M 5/31535; A61M 2005/2488

USPC .................. 604/207–211, 232, 234, 310, 311
See application file for complete search history.

(56) References Cited

U.S. PATENT DOCUMENTS

| | | | |
|---|---|---|---|
| 3,302,462 A | | 2/1967 | Pursell |
| 5,383,865 A | * | 1/1995 | Michel .......................... 604/232 |
| 5,423,752 A | | 6/1995 | Haber et al. |
| 5,514,097 A | | 5/1996 | Knauer |
| 5,584,815 A | | 12/1996 | Pawelka et al. |
| 5,591,136 A | | 1/1997 | Gabriel |
| 5,792,117 A | | 8/1998 | Brown |
| 5,820,602 A | | 10/1998 | Kovelman et al. |
| 6,090,080 A | | 7/2000 | Jost et al. |
| 6,936,032 B1 | | 8/2005 | Bush, Jr. et al. |

(Continued)

FOREIGN PATENT DOCUMENTS

| | | |
|---|---|---|
| DE | 93 01 334 U1 | 4/1993 |
| DE | 197 30 999 C1 | 12/1998 |

(Continued)

OTHER PUBLICATIONS

Machine Deisgn, Penton Media, vol. 65, No. 11 (1993) p. 36 "Standard Compression Springs Save Space".

*Primary Examiner* — Theodore Stigell
(74) *Attorney, Agent, or Firm* — McDonnell Boehnen Hulbert & Berghoff LLP (57) ABSTRACT

A resettable dosing mechanism comprises a dose button and a dial grip operatively coupled to the dose button. A spindle acts on a bung of a cartridge and a driver is operatively coupled between the dose button and the spindle. During an injection of the dose, the dose button moves in an axial direction to cause the spindle to administer the dose. During resetting of the dose setting mechanism, the spindle is retracted back into the dose setting mechanism.

4 Claims, 7 Drawing Sheets

(56) References Cited

U.S. PATENT DOCUMENTS

| | | | |
|---|---|---|---|
| 7,195,616 B2* | 3/2007 | Diller et al. | 604/224 |
| 2004/0127858 A1 | 7/2004 | Bendek et al. | |
| 2004/0162528 A1 | 8/2004 | Horvath et al. | |
| 2004/0186437 A1 | 9/2004 | Frenette et al. | |
| 2004/0210199 A1* | 10/2004 | Atterbury et al. | 604/224 |
| 2004/0236285 A1 | 11/2004 | Fisher et al. | |
| 2005/0137571 A1 | 6/2005 | Hommann | |
| 2006/0153693 A1 | 7/2006 | Fiechter et al. | |
| 2006/0258988 A1 | 11/2006 | Keitel et al. | |
| 2007/0021718 A1 | 1/2007 | Burren et al. | |
| 2007/0111175 A1 | 5/2007 | Raven et al. | |
| 2008/0027397 A1* | 1/2008 | DeRuntz et al. | 604/220 |
| 2008/0077095 A1* | 3/2008 | Kirchhofer | 604/246 |
| 2008/0208123 A1 | 8/2008 | Hommann | |
| 2009/0227959 A1 | 9/2009 | Hirschel et al. | |

FOREIGN PATENT DOCUMENTS

| | | |
|---|---|---|
| DE | 298 18 721 U1 | 3/2000 |
| DE | 10 2005 063 311 A1 | 8/2006 |
| DE | 10 2005 060 928 A1 | 6/2007 |
| DE | 10 2006 038 123 A1 | 2/2008 |
| DE | 10 2007 026 083 A1 | 11/2008 |
| EP | 0 897 728 A1 | 2/1999 |
| EP | 0 937 471 A2 | 8/1999 |
| EP | 0 937 472 A2 | 8/1999 |
| EP | 1 541 185 A1 | 6/2005 |
| EP | 1 776 975 A2 | 4/2007 |
| EP | 1 923 084 A1 | 5/2008 |
| GB | 2 443 390 A | 5/2008 |
| WO | 92/18180 A1 | 10/1992 |
| WO | 93/07922 A1 | 4/1993 |
| WO | 96/23973 A1 | 8/1996 |
| WO | 96/39214 A1 | 12/1996 |
| WO | 97/10864 A1 | 3/1997 |
| WO | 99/03520 A1 | 1/1999 |
| WO | 01/10484 | 2/2001 |
| WO | 01/19434 A1 | 3/2001 |
| WO | 02/051471 | 7/2002 |
| WO | 02/092153 | 11/2002 |
| WO | 03/080160 A1 | 10/2003 |
| WO | 2004/020028 A1 | 3/2004 |
| WO | 2004/030730 | 4/2004 |
| WO | 2004/047893 | 6/2004 |
| WO | 2004/064900 | 8/2004 |
| WO | 2004/064902 A1 | 8/2004 |
| WO | 2004/078241 A1 | 9/2004 |
| WO | 2004/078242 A2 | 9/2004 |
| WO | 2004/078293 A1 | 9/2004 |
| WO | 2005/018721 A1 | 3/2005 |
| WO | 2005/021072 A1 | 3/2005 |
| WO | 2005/039676 | 5/2005 |
| WO | 2005/044346 A2 | 5/2005 |
| WO | 2005/123159 A2 | 12/2005 |
| WO | 2006/024461 A1 | 3/2006 |
| WO | 2006/058883 A2 | 6/2006 |
| WO | 2006/079481 A1 | 8/2006 |
| WO | 2006/089767 A1 | 8/2006 |
| WO | 2006/114395 A1 | 11/2006 |
| WO | 2006/125328 A1 | 11/2006 |
| WO | 2007/017052 A1 | 2/2007 |
| WO | 2007/067889 A1 | 6/2007 |
| WO | 2008/031235 A1 | 3/2008 |
| WO | 2008/074897 A1 | 6/2008 |
| WO | 2008/116766 A1 | 10/2008 |
| WO | 2008/128373 A1 | 10/2008 |

* cited by examiner

RESETTABLE DRUG DELIVERY DEVICE

FIELD OF THE PRESENT PATENT APPLICATION

The present application is generally directed to dose setting mechanisms for drug delivery devices. More particularly, the present application is generally directed to resettable dose setting mechanisms for drug delivery devices.

Pen type drug delivery devices provide for self administration of medicinal product from a multi-dose cartridge. A resettable pen type drug delivery device allows a user to replace an empty multi-dose cartridge with a new cartridge. Consequently, the user is called upon to re-set a dose setting mechanism of the drug delivery device. Aspects of the invention may be equally applicable in other scenarios as well.

BACKGROUND

Pen type drug delivery devices have application where regular injection by persons without formal medical training occurs. This is increasingly common among patients having diabetes where self-treatment enables such patients to conduct effective management of their disease.

Pen type drug delivery devices have application where regular injection by persons without formal medical training occurs. This may be increasingly common among patients having diabetes where self-treatment enables such patients to conduct effective management of their disease.

There are basically two types of pen type delivery devices: resettable devices (i.e., reusable) and non-resettable (i.e., disposable). These types of pen delivery devices (so named because they often resemble an enlarged fountain pen) are generally comprised of three primary elements: (i) a cartridge section that includes a cartridge often contained within a housing or holder; (ii) a needle assembly connected to one end of the cartridge section; and (iii) a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then a dose is administered. Such removable needle assemblies may be threaded onto, or pushed (i.e., snapped) onto the pierceable seal end of the cartridge assembly.

The dosing section or dose setting mechanism is typically the portion of the pen device that is used to set a dose. During an injection, a spindle contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

Different types of pen delivery devices, including disposable (i.e., non-resettable) and reusable (i.e., resettable) varieties, have evolved over the years. For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism.

In contrast to typical disposable pen type devices, typical reusable pen delivery devices feature essentially two main reusable components: a cartridge holder and a dose setting mechanism. After a cartridge is inserted into the cartridge holder, this cartridge holder is attached to the dose setting mechanism. The user uses the dose setting mechanism to select a dose. Before the user injects the set dose, a replaceable double-ended needle assembly is attached to the cartridge housing. This needle assembly may be threaded onto or pushed onto (i.e., snapped onto) a distal end of the cartridge housing. In this manner, a double ended needle mounted on the needle assembly penetrated through a pierceable seal at a distal end of the cartridge. After an injection, the needle assembly is removed and discarded. After the insulin in the cartridge has been exhausted, the user detaches the cartridge housing from the dose setting mechanism. The user can then remove the empty cartridge from the cartridge retainer and replace the empty cartridge with a new (filled) cartridge. Aside from replacing the empty cartridge with a new cartridge, the user must somehow prepare the dose setting mechanism for a new cartridge: the dose setting mechanism must be reset to a starting or initial position. For example, in certain typical resettable devices, in order to reset the dose setting mechanism, the spindle that advances in a distal direction during dose injection must somehow be retracted back into the dose setting mechanism. Certain known methods of retracting this spindle back into the dose setting mechanism to a restart or an initial position are known in the art. As just one example, known reset mechanisms require a user to turn back or push back (retract) the spindle or some other portion of the dose setting mechanism.

Resetting of known dose setting mechanisms have certain perceived disadvantages. One perceived disadvantage is that the pen device user has to disassemble the device to either remove an empty cartridge or somehow reset the device. As such, another perceived disadvantage is that such devices have a high number of parts and therefore such devices are typically complicated from a manufacturing and from an assembly standpoint. For example, certain typical resettable pen type devices are not intuitive as to how a user must replace an empty cartridge and reset the device. In addition, because such resettable devices use a large number of components parts, such resettable devices tend to be large and bulky, and therefore not easy to carry around or easy to conceal.

There is, therefore, a general need to take these disadvantages associated with resetting issues into consideration in the design and development of resettable drug delivery devices. Such desired drug delivery devices would tend to reduce the number of component parts and also tend to reduce manufacturing costs while also making the device less complex to assemble and manufacture. Such desired devices would also tend to simplify the steps required for a user to reset a dose setting mechanism while also making the device less complex and more compact in size.

SUMMARY

According to an exemplary embodiment, a resettable dosing mechanism comprises a dose button and a dial grip operatively coupled to the dose button. A spindle acts on a bung of a cartridge and a driver is operatively coupled between the dose button and the spindle. During an injection of the dose, said dose button moves in an axial direction to cause said spindle to administer said dose. During resetting of the dose setting mechanism, the spindle is retracted back into the dose setting mechanism. In another exemplary embodiment, a resettable dose setting mechanism comprises an inner housing having a helical groove. A dose dial sleeve is rotationally engaged with the helical groove. A driver is provided within the inner housing. A clutch is provided between the inner housing member and the driver. When a dose is set, the clutch engages and the dial sleeve and the driver rotate together. When the dose is injected, the clutch disengages the dose dial sleeve from the driver while the clutch couples the driver to the inner housing, so that the dose dial sleeve rotates and the driver is prevented from rotating but moves axially against a spindle to expel the set dose. When resetting the dose setting mechanism, the clutch decouples the driver from the dial sleeve, allowing the driver to be moved to a reset position.

In yet another arrangement, a resettable drug delivery device comprises a cartridge holder comprising a releasable mechanical interlock. A resettable dose setting mechanism is releasably coupled to the interlock. The dose setting mechanism comprises a dose button, a transfer sleeve, and a rotatable dose setting sleeve. When the dose setting sleeve is rotated to reach a predetermined position, the dose setting sleeve releases the mechanical interlock and places the resettable dose setting mechanism in a reset condition.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Figures 1, 2:
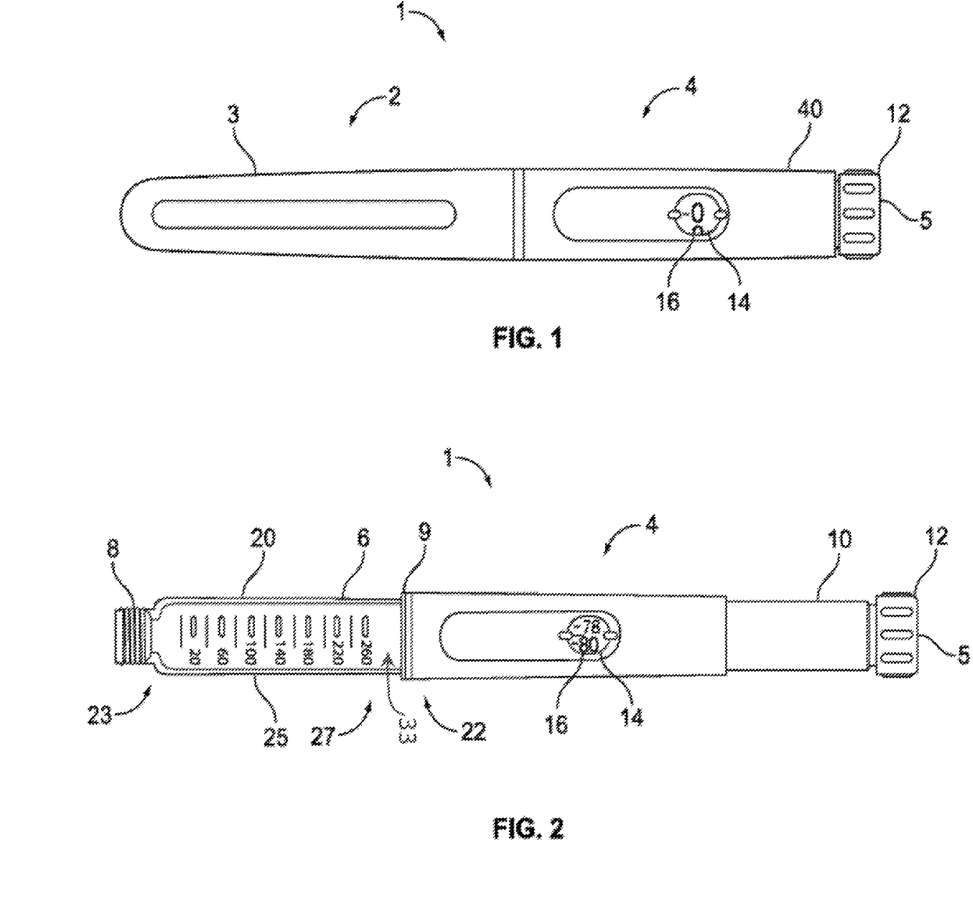
FIG. 1 illustrates a first embodiment of a resettable drug delivery device.
FIG. 2 illustrates the resettable drug delivery device of FIG. 1 with the cap removed and with a dose having been dialed.

Referring to FIG. 1, there is shown a drug delivery device 1 in accordance with an exemplary arrangement. The drug delivery device 1 comprises a housing having a first cartridge retaining part 2, and a dose setting mechanism 4. The drug delivery device is a resettable drug delivery device (i.e., a reusable device). A first end of the cartridge retaining part 2 and a second end of the dose setting mechanism 4 are secured together by connecting features. For this resettable device, these connecting features are releasable connecting features such as a thread or other similar connecting features.

In this illustrated arrangement, the cartridge housing 2 is secured within the second end of the dose setting mechanism 4. A removable cap 3 is releasably retained over a second end or distal end of a cartridge retaining part or cartridge housing. The dose setting mechanism 4 comprises a dose dial grip 12 and a window or lens 14. A dose scale arrangement 16 is viewable through the window or lens 14. To set a dose of medication contained within the drug delivery device 1, a user rotates the dose dial grip 12 such that a dialed dose will become viewable in the window or lens 14 by way of the dose scale arrangement 16.

FIG. 2 illustrates the medical delivery device 1 of FIG. 1 with the cover 3 removed from a distal end 19 of the medical delivery device 1. This removal exposes the cartridge housing 6. As illustrated, a cartridge 25 from which a number of doses of a medicinal product may be dispensed, is provided in the cartridge housing 6.

Preferably, the cartridge 25 contains a type of medicament that can be administered relatively often, such as once or more times a day. One such medicament is either long acting or short acting insulin or an insulin analog. The cartridge 25 comprises a bung or stopper (not illustrated in FIG. 2) that is retained near a second end or a proximal end 27 of the cartridge 25. The medical delivery device also comprises a driver having a spindle (not illustrated in FIG. 2).

The cartridge housing 6 has a distal end 23 and a proximal end 27. Preferably, the cartridge distal end 23 of the cartridge housing 6 comprises a groove 8 for attaching a removable needle assembly. However, other needle assembly connection mechanisms could also be used. The cartridge proximal end 27 is removably connected to the dose setting mechanism 4. In one preferred embodiment, cartridge housing proximal end 27 is removably connected to the dose setting mechanism 4 via a bayonet connection. However, as those of ordinary skill in the art will recognize, other types of removable connection methods such as threads, partial threads, ramps and detents, snap locks, snap fits, and luer locks may also be used.

The cartridge 25 is removable from the cartridge housing 6. The cartridge 25 may be removed from the device 1 without destroying the device 1 by merely having the user disconnect the dose setting mechanism 4 from the cartridge housing 6.

In use, once the cap 3 is removed, a user can attach a suitable needle assembly to the groove 8 provided at the distal end 23 of the cartridge housing 6. Such needle assembly may be, for example, screwed onto a distal end 23 of the housing 6 or alternatively may be snapped onto this distal end 23. After use, the replaceable cap 3 may be used to re-cover the cartridge housing 6. Preferably, the outer dimensions of the replaceable cap 3 are similar or identical to the outer dimensions of the dose setting mechanism 4 so as to provide an impression of a unitary whole when the replaceable cap 3 is in position covering the cartridge housing 6 when the device is not in use.

Figure 3:
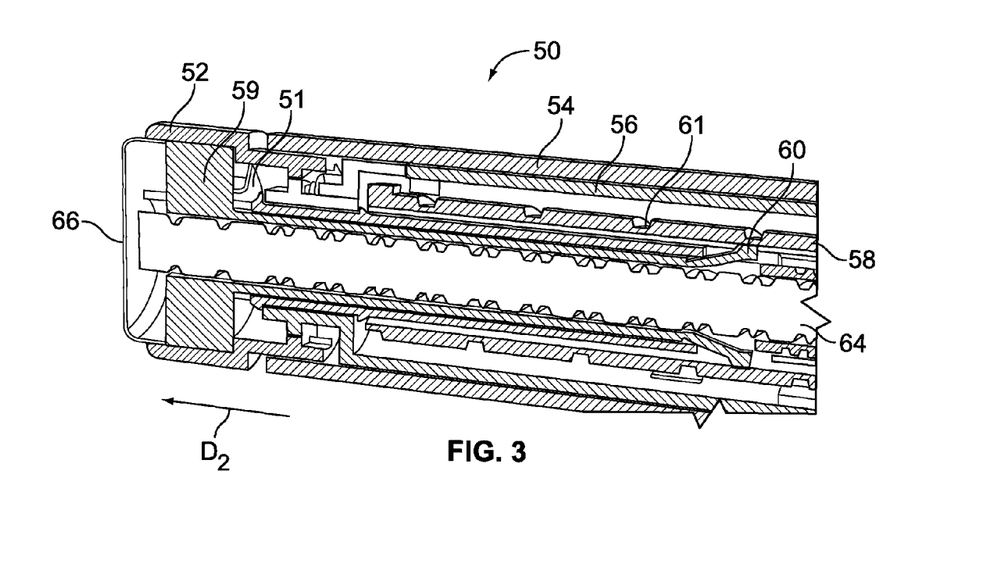
FIG. 3 illustrates a sectional view of a first arrangement of a dose setting mechanism, such as the dose setting mechanism of the drug delivery device illustrated in FIG. 1.
Figure 4:
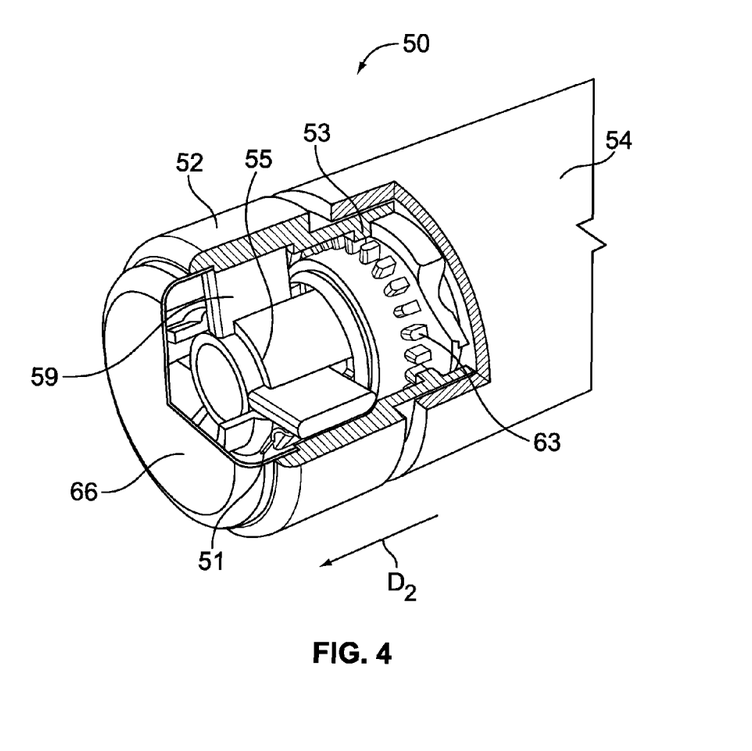
FIG. 4 is a partial perspective view of the dose setting mechanism illustrated in FIG. 3.

FIG. 3 illustrates a cross sectional view of a first arrangement of a dose setting mechanism 50, such as the dose setting mechanism 4 illustrated in FIG. 2. Those of skill in the art will recognize that dose setting mechanism 50 may include a connection mechanism for releasably connecting to a cartridge holder, like the cartridge holder 6 illustrated in FIG. 2. FIG. 4 is a partial perspective view of the dose setting mechanism illustrated in FIG. 3.

With reference to FIGS. 3 and 4, the dose setting mechanism 50 comprises a button 66, a dose dial grip 52, a spring 51, an outer housing 54, a clutch sleeve 59, a driver 55, a dial sleeve 56, an inner housing 58, and a spindle 64. As clearly seen from FIG. 4, the driver 55 is coupled to the clutch sleeve 59.

As illustrated, the outer housing 54 surrounds the various components making up the dose setting mechanism 50. The inner housing 58 has an outer surface comprising a helical groove 61. The dial sleeve 56 comprises a male groove member 62 that engages the helical groove 61. Because of this rotational engagement, during a dose setting step, the dial sleeve 56 translates along this groove 61 in a proximal direction. In addition, the driver 55 is threadedly engaged with a portion of the spindle such that when the driver 55 is urged in a distal direction, the spindle is likewise urged in a distal direction.

In addition, the dial sleeve 56 further comprises a set of circumferential teeth 63 that radiate out away from the dial sleeve. These circumferential teeth 63 are releasably coupled to a portion of the dose dial grip 52. In one preferred arrangement, the circumferential teeth 63 of the dial sleeve 56 releasably engage inner directed corresponding teeth 53 along a distal portion of the dose dial grip 52. The engagement of the two sets of teeth 53, 63 can be clearly seen from FIG. 4.

Consequently, in the position illustrated in FIG. 4, rotation of the dose dial grip 52 will in turn rotate both the driver 55 and the clutch sleeve 59. Since the clutch sleeve 59 is engaged with both the driver 55 and the dial sleeve 56, rotation of the dose dial grip 52 will result in relative rotation of the dial sleeve 56 as well. Rotation of the dial sleeve 56 causes a dose to be set, similar to the dose set with the drug delivery device 1 illustrated in FIG. 1.

Returning to FIG. 5, the spindle 64 is threadedly engaged with a portion of the inner housing 58. In this manner, an axial force on the spindle 64 in the distal direction causes the spindle 64 to rotate due to this threaded connection. This rotation and axial movement of the spindle 64 is caused by an axial force applied by the driver 55 on to the spindle 64 via a threaded engagement as the driver moves axially towards the distal end of the dose setting mechanism 50.

Figure 5:
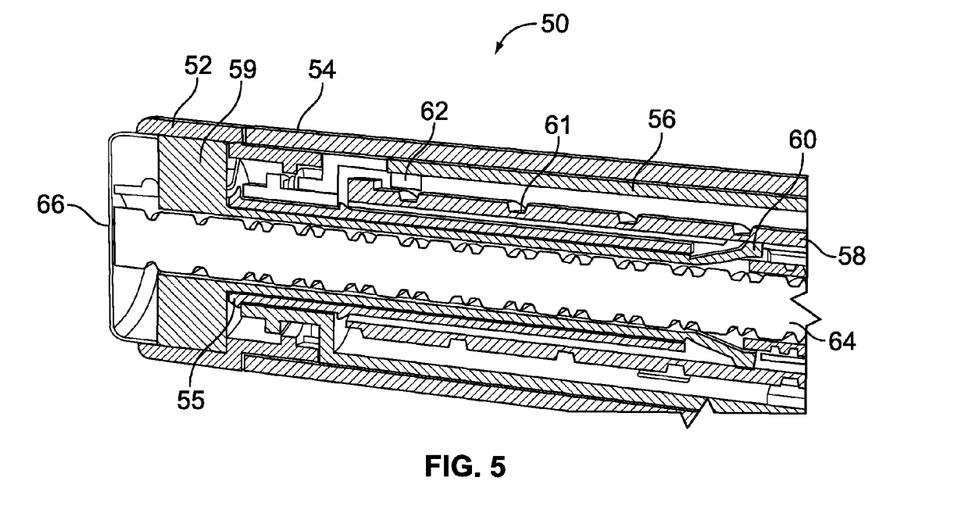
FIG. 5 illustrates a sectional view of the dose setting mechanism illustrated in FIG. 3 in a dose dialing state.

The clutch sleeve 59 is prevented from disengaging the driver 55 since the clutch sleeve 59 is splined to the driver 55 preventing relative rotation between these two components. During dispense the clicker 60 is locked in splined engagement to the inner housing 58. Therefore, the driver 55 cannot rotate relative to either the inner housing 58, the clutch sleeve 59 or the dial grip 52. The dial sleeve 56 can rotate relative to the driver 55 since the clutch teeth 53, 63 are disengaged. As a consequence, the dial sleeve 56 can rotate relative to the outer housing 54 and the inner housing 58.

Figure 6:
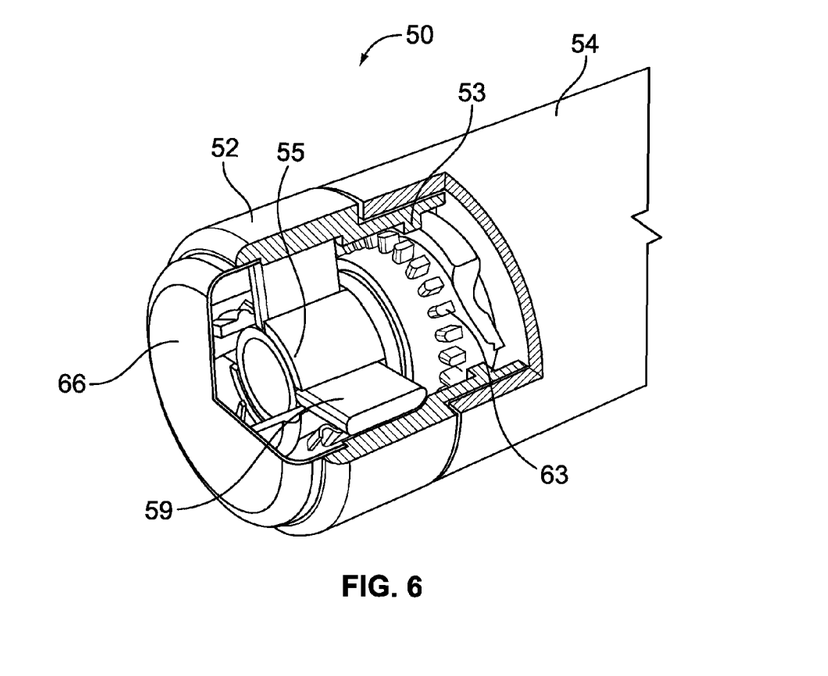
FIG. 6 is a partial perspective view of the dose setting mechanism illustrated in FIG. 5.

FIG. 5 illustrates the dose setting mechanism 50 illustrated in FIG. 3 in a dose dispensing state (i.e., during the injection of a previously dialed dose). FIG. 6 is a partial perspective view of the dose setting mechanism illustrated in FIG. 5. Referring now to both FIGS. 5 and 6, when the previously set dose is being dispensed, the user applies an axial load to the dose button 66. The dose button 66 is axially coupled to the clutch sleeve 59 and this coupling prevents relative axial movement. Therefore, the clutch sleeve 59 moves axially towards the cartridge end or the distal end of the dose setting mechanism 50. This movement disengages the clutch sleeve 59 from the dial sleeve 56. For example, as can be clearly seen from FIG. 6, axial movement of the button 66 moves the dose dial grip 52 in the distal direction D1. Specifically, movement of the dose dial grip 52 in this distal direction disengages the outwardly directed teeth 63 of the dial sleeve 56 from the inwardly radial extending teeth 53 of the dose dial grip 52. Disengaging these two components allows for the relative rotation of the dial sleeve 56 with respect to the outer housing 54 the clutch sleeve 59 and driver 55.

As described above, the clutch sleeve 59 is now prevented from rotating relative to the inner housing 58 since the clicker 60 is locked in splined engagement with the inner housing 58. However, in this scenario, the clutch 59 remains engaged with the driver 55.

Figure 7:
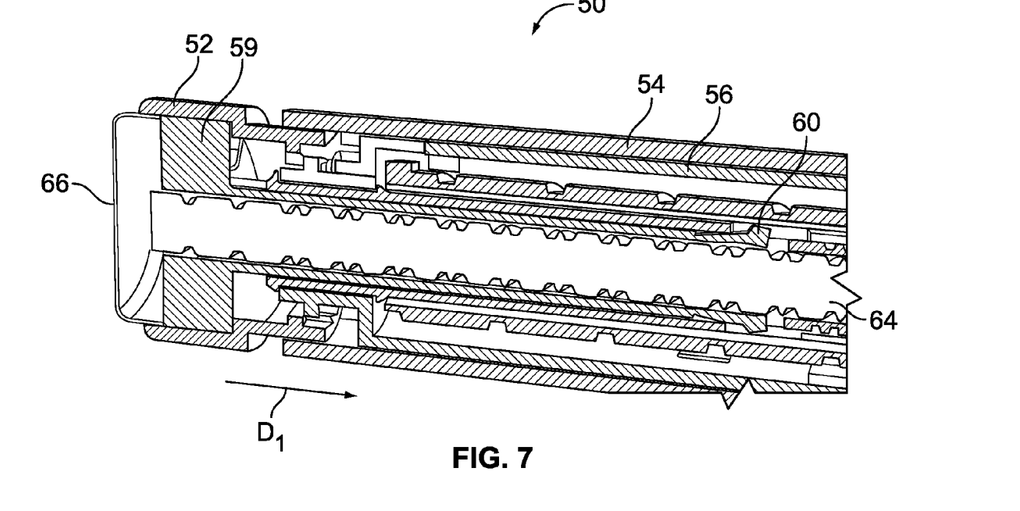
FIG. 7 illustrates a sectional view of the dose setting mechanism illustrated in FIG. 5 in an initial device resetting condition.
Figure 8:
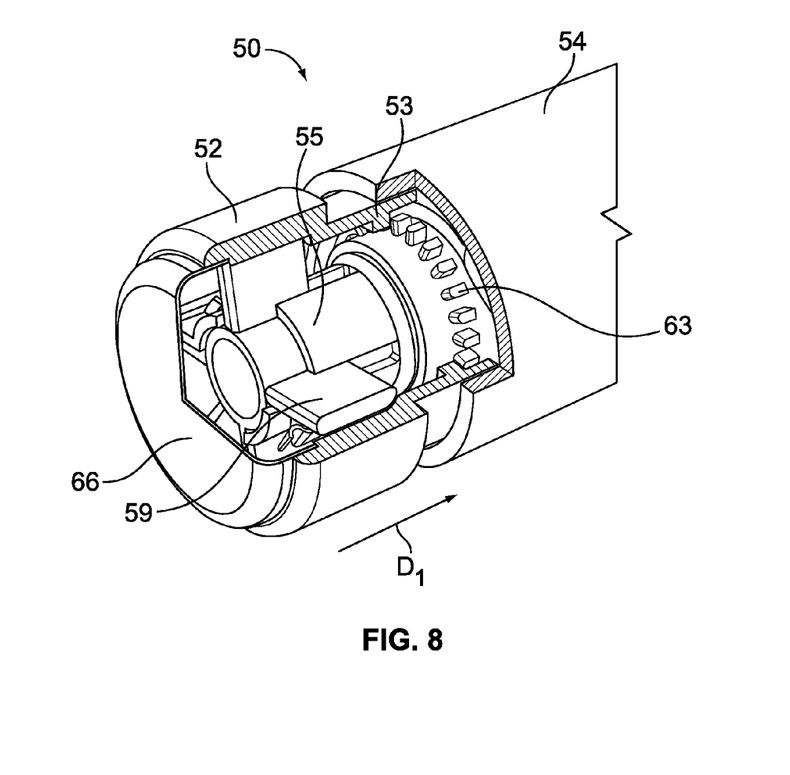
FIG. 8 is a partial perspective view of the dose setting mechanism illustrated in FIG. 7.

FIG. 7 illustrates the dose setting mechanism 50 illustrated in FIGS. 5 and 6 in a reset condition. FIG. 8 provides a close up illustration of the driver 55 rotationally decoupled from the dial sleeve 56 as illustrated in FIG. 7. Referring now to both FIGS. 7 and 8, in this reset condition, a user must first rotate the dial grip to an initial starting position before the dose dial grip 52 is pulled in a proximal direction D2 to retract and rotate the spindle back into the dose setting mechanism. That is, the user pulls the dose dial grip away from the dose setting mechanism 50. This axial movement of the dose dial grip 52 allows the driver 55 and the dial sleeve 56 to become decoupled in rotation. This allows the driver 55 to rotate independently of the dial sleeve 56. The driver 55 and the inner housing 58 also become decoupled in rotation. In one preferred arrangement, a clicker portion 60 of the clutch sleeve 59 is retracted from a spline provided in the inner housing 58. As shown in FIGS. 7 and 8, a user is required to pull in the proximal direction D2 the dose button 66 to place the dose setting mechanism 50 into a reset condition. Since the clutch sleeve 59 and driver 55 are free to rotate independently of the dial sleeve 56, the dose setting mechanism 50 may be reset by retracting the spindle 64 back into the dose setting mechanism 50. This can be accomplished by the user pushing the spindle 64 in the proximal direction D2. This re-sets the dose setting mechanism 50.

In one preferred arrangement, a detent mechanism is provided to retain the clutch sleeve 59, dial grip 52 and driver 55 in this reset condition illustrated in FIGS. 7 and 8. This detent mechanism preferably retains the clutch sleeve 59, dial grip 52 and driver 55 in this reset condition until a user presses the dose button 66 back in a distal direction, D1 (see, e.g., FIG. 3).

In this preferred arrangement illustrated in FIGS. 3-8, a user is required to pull out the dose button to place the device into a reset condition. Once in the reset condition, the driver may be manipulated or rotated back to an initial start condition and then the spindle can be retracted back into the dose setting mechanism.

Figure 9:
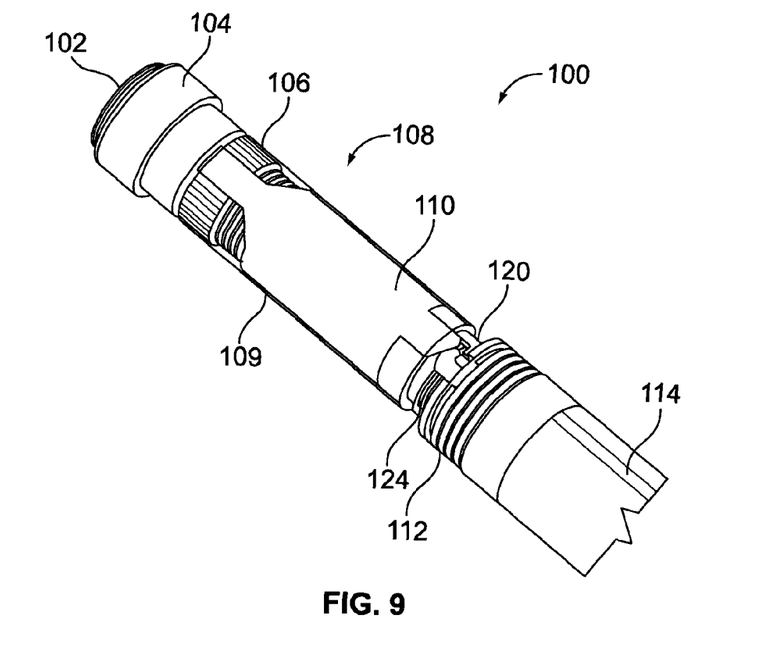
FIG. 9 illustrates a second arrangement of a drug delivery device according to one aspect of the present invention.

FIG. 9 illustrates a second arrangement of a drug delivery device 100 according to one aspect of the present invention. The reset function of the drug delivery device 100 is different than that of the dose setting mechanism illustrated in FIGS. 3-8. For example, whereas the resetting function of the dose setting mechanism 50 is a manual operation, the resetting function of the drug delivery device 100 is semiautomatic.

The mechanical structure of the dose setting mechanism 108 is similar to the operation of the dose setting mechanism 50 illustrated in FIGS. 3-8. For example, the dose setting operation illustrated in FIGS. 3-4 and the dose administration operation illustrated in FIGS. 5-6 apply equally as well to how the dose setting mechanism 108 sets and then administers a dose.

One difference between the dose setting mechanism 108 of FIG. 9 and the dose setting mechanism 50 illustrated in FIG. 3 is that mechanism 108 includes an additional array of components that releasably interlocks the dose setting mechanism 108 with the cartridge holder 114. In one preferred arrangement, a clutch of the resettable dose setting mechanism 108 (similar to the clutch 59 of dose setting mechanism 50) is placed in a reset mode automatically. Preferably, this occurs automatically when the cartridge holder 114 is removed from the dose setting mechanism 108. Consequently, in this alternative arrangement, no additional steps on behalf of the user (or a patient caregiver) is required to place the dose setting mechanism 108 in its reset condition or a reset state. For example, in this alternative arrangement, the user is not required to manually pull back the dose dial sleeve so as to enable spindle retraction.

As illustrated, this drug delivery device 100 comprises a dose setting mechanism 108 releasably connected to a cartridge holder 114. This dose setting mechanism 108 is similar in operation to the dose setting mechanism 50 illustrated in FIG. 3. This dose setting mechanism 108 comprises a dose button 102 and a dose dial grip 104 at a proximal end of the dose setting mechanism 108. This mechanism further includes an interlock collar 120, a housing 106, and a transfer sleeve 110. A dose dial sleeve 109 surrounds the transfer sleeve 110. The cartridge holder 114 comprises a removable cartridge, a spring 112, and a release sleeve 124.

Figure 10:
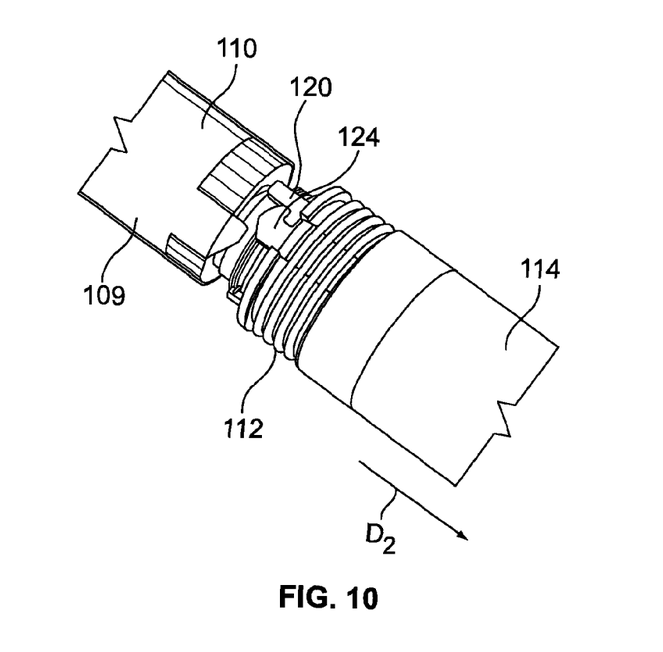
FIG. 10 illustrates the dose dial sleeve of FIG. 9 in a partially dialed out position.
Figure 11:
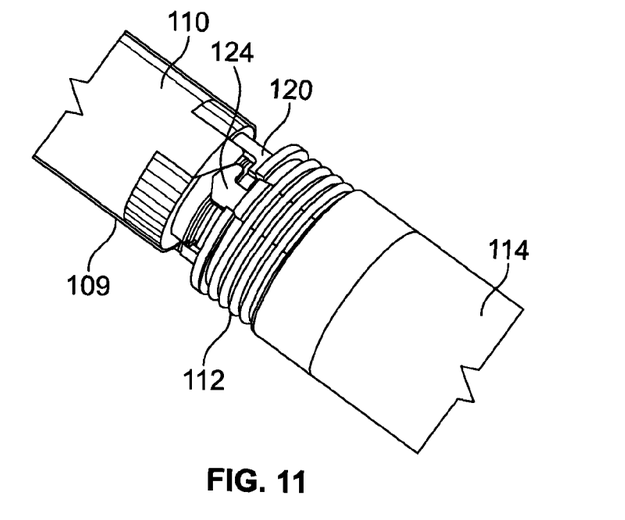
FIG. 11 illustrates the dose dial sleeve of FIG. 10 in a fully dialed in position.

FIG. 10 illustrates the dose dial sleeve of FIG. 9 in a partially dialed out position. In FIG. 10, the dial sleeve has been rotated a certain amount so as to select a dose. In this position, it can be seen that the interlock collar 120 is engaged with the release sleeve 124. This engagement prevents any movement of the release sleeve 124 in the forward or distal direction D2. Therefore, this engagement also prevents a user from removing the cartridge holder 114 from the dose setting mechanism 108. FIG. 11 illustrates the dose dial sleeve of FIG. 10 in a fully dialed in position. As illustrated, the interlock collar 120 is disengaged from the release sleeve 124. This allows for forward movement of the release sleeve 124. Therefore, this disengagement also allows a user to remove the cartridge holder 114 from the dose setting mechanism 108.

Figure 12:
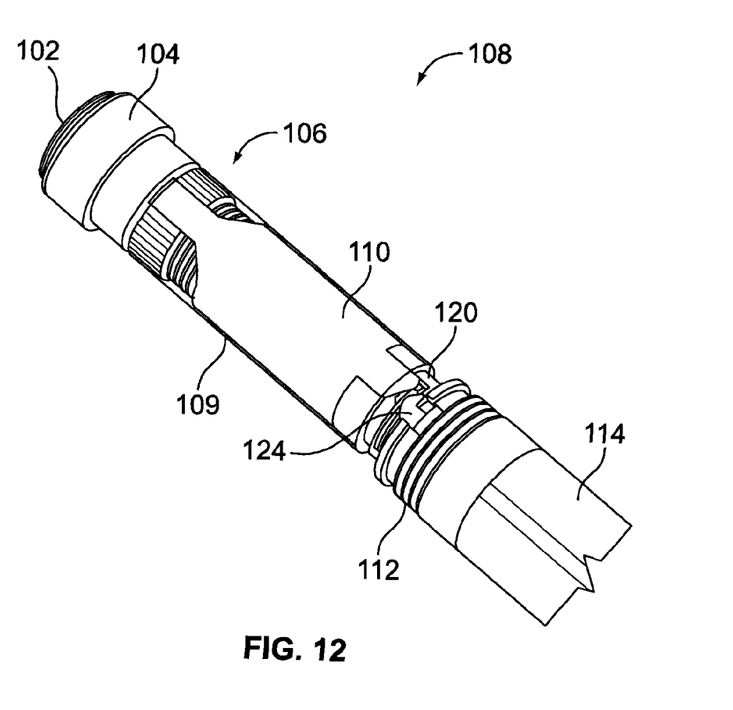
FIG. 12 illustrates an interlock collar disengaged from a release sleeve.

FIG. 12 illustrates the interlock collar 120 disengaged from the release sleeve 124. This allows for forward movement of the release sleeve 124 and hence removal of the cartridge holder 114.

Figure 13:
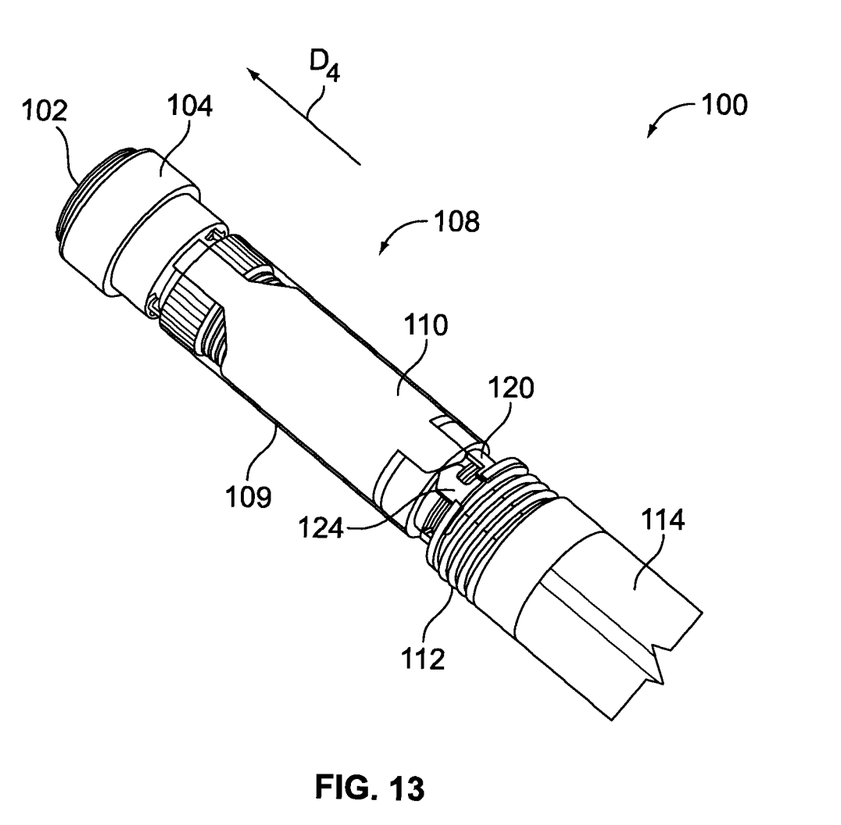
FIG. 13 illustrates the cartridge holder of FIG. 12 disengaged from the dose setting mechanism.

FIG. 13 illustrates the cartridge holder of FIG. 12 being disengaged from the dose setting mechanism 108. This also allows the release spring 112 to push the transfer sleeve 110 in a proximal direction D4. As this transfer sleeve moves in the proximal direction, it pushes the dose button 102 and places the clutch in the reset state.

When the cartridge holder 114 is removed from the dose setting mechanism 108, a release sleeve 110 is driven in the rearward or proximal direction. Preferably, this release sleeve 110 is spring loaded via a spring 112. The travel of the spring loaded release sleeve 110 causes a dose button 102 of the dose setting mechanism 108 to also move in proximal direction.

Because the dose button 102 is operatively coupled to the driver, axial movement of the dose button 102 places both the clutch and the driver in a reset state.

Consequently, as the cartridge holder 114 is removed and the dose setting mechanism 108 is automatically placed into a reset condition so that the spindle can be retracted back into the dose setting mechanism 108. The dose setting mechanism 108 may then be reset by turning the dial grip 104 that is engaged with the driver so that the driver may be rotated back to an initial starting position. Once the driver is returned to this initial position, a new cartridge containing medicament (i.e., such as a fast or slow acting insulin) may be placed in the cartridge holder which may then be reconnected to the dose setting mechanism.

Exemplary embodiments of the present concepts have been described. Those skilled in the art will understand, however, that changes and modifications may be made to these embodiments without departing from the true scope and spirit of the present concepts, which is defined by the claims.

I claim:

1. A resettable dosing mechanism for use with a resettable pen type drug delivery device, said dosing mechanism comprising:
   a dose button;
   a dial grip operatively coupled to said dose button and a dose dial sleeve that is configured to rotate during dose setting and during dose delivery, said dial grip rotatable to set a dose;
   a spindle for acting on a bung of a cartridge; and
   a driver operatively coupled to said dose button and said spindle, where the driver is engaged with the dose dial sleeve such that the driver rotates during dose setting and does not rotate during dose delivery;
   wherein during an injection of said dose, said dose button moves in an axial direction to cause said spindle to rotate and move in a distal direction to administer said dose, and
   wherein during resetting of said resettable dosing mechanism, the dial grip must be pulled by a user in a proximal direction to disengage the driver from the dose dial sleeve before the spindle can be pushed in a proximal direction and retracted back into said resettable dosing mechanism.

2. The invention of claim 1 wherein said dial grip must be rotated to an initial starting position before said dial grip can be pulled in said proximal direction to retract said spindle back into said resettable dosing mechanism.

3. The invention of claim 1 wherein said resettable dosing mechanism is removably connected to a cartridge holder.

4. The invention of claim 1 wherein when said spindle is retracted back into said resettable dosing mechanism, said spindle rotates.

* * * * *